United States Patent [19]

Dilla et al.

[11] Patent Number: 5,393,428
[45] Date of Patent: Feb. 28, 1995

[54] PROCESS FOR TREATING WASTE WATER CONTAINING CHLORINATED ORGANIC COMPOUNDS FROM PRODUCTION OF EPICHLOROHYDRIN

[75] Inventors: Wolfgang Dilla; Helmut Dillenburg; Erich Ploenissen, all of Rheinberg; Michael Sell, Peine, all of Germany

[73] Assignee: Solvay Deutschland GmbH, Hanover, Germany

[21] Appl. No.: 114,635

[22] Filed: Sep. 2, 1993

[30] Foreign Application Priority Data

Sep. 6, 1992 [DE] Germany .............................. 4229355
Sep. 6, 1992 [DE] Germany .............................. 4229356

[51] Int. Cl.⁶ .......................... C02F 1/02; C02F 1/58
[52] U.S. Cl. .................................. 210/631; 210/762; 210/766; 210/908; 210/909
[58] Field of Search ............... 210/631, 757, 761–763, 210/766, 774, 908, 909

[56] References Cited

U.S. PATENT DOCUMENTS

| | | | |
|---|---|---|---|
| 3,988,259 | 10/1976 | Ray | 210/762 |
| 4,246,104 | 1/1981 | Schmidt et al. | 210/763 |
| 4,604,215 | 8/1986 | McCorguodale | 210/762 |
| 4,869,833 | 9/1989 | Binning et al. | 210/761 |
| 5,108,647 | 4/1992 | Bölsing | 210/909 |

FOREIGN PATENT DOCUMENTS

| | | |
|---|---|---|
| 247670 | 12/1987 | European Pat. Off. . |
| 454642 | 10/1991 | European Pat. Off. . |
| 2332959 | 6/1977 | France . |
| 97184 | 4/1973 | German Dem. Rep. . |
| 254573 | 3/1988 | German Dem. Rep. . |
| 3620980 | 1/1988 | Germany . |
| 51-5864 | 1/1976 | Japan . |
| 63-158188 | 7/1988 | Japan . |
| WO92/05118 | 4/1992 | WIPO . |

OTHER PUBLICATIONS

Roempps Chemie-Lexikon, pp. 2485–2486.

*Primary Examiner*—Thomas Wyse
*Attorney, Agent, or Firm*—Evenson, McKeown, Edwards & Lenahan

[57] ABSTRACT

A process for treating waste water containing chlorinated organic substances, particularly waste water from production of epichlorohydrin which contains more than 10 mg of adsorbable organic halogen compounds (AOX) per liter, comprising charging the waste water at a pH of 10 to 14 (measured at room temperature) into a reactor and maintaining a temperature of at least 75°C., a pressure of at least 1 bar (abs.), and a residence time of at least 0.5 hours in said reactor, thereby partially dechlorinating and/or dehydrochlorinating chlorinated organic compounds contained in the waste water, and thereafter subjecting the waste water to further dechlorination and/or dehydrochlorination treatment in the presence of a hydrogen-containing gas, a hydrogen-releasing compound and/or a catalytically active material; and optionally subjecting the waste water to a biological treatment with the use of microorganisms; and apparatus for carrying out the foregoing process.

14 Claims, 1 Drawing Sheet

PROCESS FOR TREATING WASTE WATER CONTAINING CHLORINATED ORGANIC COMPOUNDS FROM PRODUCTION OF EPICHLOROHYDRIN

BACKGROUND OF THE INVENTION

The present invention relates to a process for treating organic substances, particularly waste waters containing chlorinated organic compounds from the production of epichlorohydrin. In this case, the epichlorohydrin obtained by the reaction of dichloropropanol with at least one compound having an alkaline effect, preferably a calcium-hydroxide-containing aqueous solution or suspension, is separated from the reaction mixture by distillation, and a waste water remains as the bottom product which contains saturated and/or unsaturated aliphatic and/or alicyclic chlorinated hydrocarbons, chlorinated ethers, chlorinated alcohols, chlorinated ketones, chlorinated aldehydes and/or chlorinated carboxylic acids. Furthermore, the present invention relates to an apparatus for carrying out this process.

Epichlorohydrin (1-chloro-2,3-epoxy-propane) produced industrially by known processes involving dehydrochlorination of dichloropropanol with agents having an alkaline effect, preferably aqueous solutions or suspensions of calcium hydroxide or sodium hydroxide, at elevated temperatures. The dichloropropanol starting material is preferably obtained as an aqueous solution of the 1,3- and 2,3-dichloropropanol isomer mixture by the reaction of allyl chloride, chlorine and water.

The epichlorohydrin formed according to the abovementioned process is separated from the reaction mixture by distillation, preferably steam distillation. In this case, an aqueous solution or suspension flows out of the synthesis reactor as the bottom product and, in addition to small quantities of the reaction product, contains further organic compounds, particularly chlorinated organic and inorganic compounds, as by-products of the synthesis as well as unreacted starting material. This bottom product, which occurs as waste water (when calcium hydroxide is used in the epichlorohydrin synthesis as the agent with the alkaline effect), typically contains the following compounds: chlorinated cyclic or acyclic alkanes and alkenes, saturated and/or unsaturated chlorinated aliphatic and/or alicyclic ethers, chlorinated alcohols, chlorinated ketones, chlorinated aldehydes and/or chlorinated carboxylic acids as well as, in addition to other compounds which contribute to the chemical oxygen demand (COD) of the waste water, particularly glycerin and glycerin derivatives, additional calcium chloride, calcium carbonate and possibly excess calcium hydroxide.

The chlorinated organic compounds contained in the bottom product contribute to the overall AOX (adsorbable organic halogen compounds) parameter of the waste water. The AOX is determined as that part of organic halogen compounds (X=F, Cl, Br, I) which can be adsorbed on activated carbon, in which case the entire adsorbed quantity is converted to X=Cl.

Waste waters of this type which contain halogenated organic compounds present a special problem in waste water treatment because, as a result of the high stability of the covalent halocarbon compounds, particularly in the case of $sp^2$-bound halogens, removal of these substances requires such high technical expenditures that it is frequently uneconomical.

Known measures for decreasing the content of chlorinated and other halogenated organic substances in waste water include chemical-physical as well as biotechnological processes.

The decomposition of halogenated organic compounds in a biochemical treatment phase in a waste water treatment facility presents various problems: On the one hand, many of these compounds exhibit little or no susceptibility to biological decomposition by means of microorganisms. On the other hand, the concentrations of AOX-generating substances in waste water must not be high and, in addition, should have largely constant values. Furthermore, the volume of activated sludge in facilities of this type is large, and the accumulation of the organic halogen compounds in the sludge presents another problem.

In the prior art, processes for chemical-physical removal of halogen-organic compounds from waste water are therefore preferably suggested, these processes being used as the primary treatment or as a preliminary treatment (with a subsequent biochemical treatment) of the waste water.

Methods which are available include, for example, activated-carbon purification as well as special extraction processes. One disadvantage of these processes is that they produce a secondary product which is contaminated with halogenated organic compounds (loaded activated carbon or extracting agents).

Frequently used measures for eliminating halogenated organic compounds in waste water include chemical-thermal processes. These include the so-called wet-oxidative processes in which halogenated organic compounds are decomposed in an oxidizing atmosphere at high temperatures and substantially elevated pressures. Although this method is very effective, it is also very cost-intensive because of the high energy consumption and the expensive equipment required.

To reduce the extreme physical conditions of chemical-thermal processes, the prior art suggests the use of catalytically active compounds, in which case such substances may be introduced into the system which is to be dehalogenated either through addition of corresponding reagents or they may form as intermediate products during the decomposition reaction.

Certain metals, metallic hydrides or metallic alcoholates, individually or in combination with a strong inorganic base, for example, are used as substances which have a high reactivity with respect to organically bound halogens.

One disadvantage of the known chemical-physical processes for the decomposing or destroying halogenated organic compounds relates to their relatively high cost which results particularly from the consumption of expensive reagents and from the provision of an oxidizing or inert atmosphere as well as relatively high temperatures and pressures and from the related requirement of expensive equipment. In addition, when the economic efficiency of the known methods for the dehalogenation and/or dehydrohalogenation of halogen-organic compounds is calculated, the often long reaction times (often more than ten hours) and the frequently only moderate decomposition rates have an unfavorable effect.

Furthermore, processes for treating waste waters from pulp bleaching are known in which the lignin chloride compounds contained in the waste water are partially dehalogenated and/or dehydrohalogenated while maintaining certain temperatures, pH-values and residence times. Correspondingly, an expensive three-step process is known from published German Patent Application No. DE 3,620,980 which envisions a preliminary treatment of the waste water by precipitation methods and a thermal hydrolysis step involving a pH setting of 11.5 with lime water and/or NaOH, a temperature setting of from 40° to 70° C., and a residence time of from 1 to 3 hours. According to PCT Patent Application No. WO 92/05118, the decomposition of lignin chloride compounds is carried out at pH-values of from 6 to 11, at temperatures of from 90° to 150° C., an overpressure of from 70 to 475 kPa during a residence time of from 2 to 5 minutes, in which case, however, AOX decomposition rates of more than 60% may be obtained, preferably with the use of additional chemical reagents or by a targeted mixing of different waste waters from pulp bleaching (in which case catalytic processes probably play a role).

The processes suggested here contain no reference to their possible use in treating waste waters from the synthesis of epichlorohydrin. In addition, it is impossible to use the aforementioned methods for decomposing lignin chloride compounds in waste water from pulp bleaching in a treatment process for waste waters from the synthesis of epichlorohydrin, since AOX decomposition rates of over 50% cannot be achieved in this manner because of the completely different composition of the waste waters and the therefore non-transferable parameters with respect to the pH-value, the temperature, the pressure and the residence time.

Thus, there exists an urgent requirement for at least partially removing the chlorinated organic compounds which occur in the waste water of a facility for the synthesis of epichlorohydrin in order to meet environmental goals. This requirement is documented in various patent applications in this technical field, for example, in published European Patent Application No. EP 247,670; in published German Patent Application No. DE 3,016, 667; and in published German Patent Application No. DE 3,520,019. However, the processes suggested in these prior patents either comprise high-cost purification stages for separating the undesired chlorinated organic compounds, or they modify the process for producing epichlorohydrin to such an extent that the amount of formed chlorinated organic by-products can be minimized. In each case, the proposed measures which are cost-intensive and often result in an only unsatisfactory reduction of the organic chlorine compounds in the waste water.

Thus, taking into consideration the aforementioned prior art, there remained a need for an economical process for removing halogenated organic compounds from industrial waste water which could be implemented with low technical expenditures, was as simple as possible to carry out, consumed low amounts of reagent chemicals, and produced high AOX decomposition rates at lower temperatures and pressures as well as short residence times. In particular, there remained a need for a process for treating waste water from the synthesis of epichlorohydrin.

SUMMARY OF THE INVENTION

It is therefore an object of the present invention to provide a process for the dechlorination treatment and/or dehydrochlorination treatment of waste waters loaded with chlorinated organic compounds from the synthesis of epichlorohydrin.

Another object of the invention is to provide a process for treating waste water containing chlorinated organic compounds which is simple to implement.

It is also an object of the invention to provide a process for treating waste water containing chlorinated organic compounds which requires only low expenditures for energy and equipment and uses low amounts of additional reagents.

A further object of the invention is to provide a process for treating waste water containing chlorinated organic compounds which can be readily carried out on a large scale basis and is ecologically acceptable.

Yet another object of the invention is to provide a process for treating waste water containing halogenated organic compounds which includes a purification process for reprocessing residues generated during the process.

These and other objects of the invention are achieved by providing a process for treating a liquid containing more than 10 mg of adsorbable organic halogen compounds (AOX) per liter comprising the steps of introducing said liquid at a pH of 10 to 14 (measured at room temperature) into a reactor and in a first treatment step maintaining a temperature of at least 75° C., a pressure of at least 1 bar (abs.) and a residence time of at least 0.5 hours in said reactor, thereby partially dechlorinating or dehydrochlorinating chlorinated organic compounds contained in the liquid; subsequently subjecting said liquid in a second treatment step to a further dechlorination or dehydrochlorination treatment in the presence of a hydrogen-containing gas, a compound which releases hydrogen or a catalytically active substance, and discharging the treated liquid.

In accordance with further aspects of the invention, the objects are also achieved by providing an apparatus for treating waste water containing chlorinated organic compounds, said apparatus comprising at least one separator, at least one heating device, at least one heat exchanger, and at least one reactor, wherein at least one of said separator and said at least one reactor comprises a conically-shaped section.

DETAILED DESCRIPTION OF PREFERRED EMBODIMENTS

The invention therefore relates to a process which is characterized in that the waste water flowing or discharged out of the reaction vessel contains adsorbable organic halogen compounds (AOX) in an amount of more than 10 mg/liter, preferably more than 20 mg/liter, and is subjected to an at least two-step dechlorination and/or dehydrochlorination treatment in that, in a first step, the waste water which has a pH-value (measured at room temperature) of 10 to 14, preferably 11 to 13 or which is adjusted to such a pH-value, is charged into and/or flows through at least one additional reactor, in which case a temperature of more than 75° C., preferably more than 85° C., a pressure of at least 1 bar (absolute), preferably at least 2 bar (absolute), and a residence time of at least 0.5 hours, preferably at least 1 hour, are set or maintained in the reactor, and the chlorinated organic compounds contained in the waste water are partially dechlorinated and/or dehydrochlorinated, and subsequently, in a second step, at least one further dechlorination and/or dehydrochlorination treatment is carried out, preferably in the presence of a hydrogen-containing gas or a hydrogen-releasing compound and/or in the presence of a catalytically active substance, and then the treated waste water is discharged from the reactor or the reactors and/or is subjected to a biological treatment using microorganisms.

The process according to the invention makes it possible to dechlorinate and/or dehydrochlorinate chlorinated organic compounds in the waste water flow of an epichlorohydrin production plant economically on a large scale and with a high decomposition rate so that the ecological and technical problems, which occur in the disposal of this waste water, can largely be solved.

In contrast to the known processes for removing halogen-organic compounds from waste waters, the process according to the invention is designed to be simpler with respect to equipment, consumes less energy and may possibly avoid the use of additional reagents in the first process. In addition, no secondary products occur which may be questionable with respect to safety regulations and/or the ecology and which then, in turn, would have to be processed or removed.

In particular, it was found that by means of the selection according to the invention of the temperature, pressure and residence time parameters of the alkaline waste water from the synthesis of epichlorohydrin, which normally has pH-values of from 11.5 to 12.5, possibly without any additional pH-rise (by the corresponding addition of basic compounds) the waste water can be subjected to the thermal dechlorination or dehydrochlorination process under alkaline conditions in accordance with a first process step, in which case, despite these relative low pH-values, surprisingly high AOX decomposition rates are achieved.

By means of the at least two-step dechlorination and/or dehydrochlorination treatment of the waste water according to the invention, if necessary, an almost complete AOX decomposition can be carried out in a cost-effective manner in that, as early as during the first step, a partial dechlorination or dehydrochlorination of the chlorinated organic compounds contained in the waste water is carried out with only limited expenditures with respect to energy and technology, and subsequently, with the use of relatively low amounts of additional reagents, a more extensive dechlorination and/or dehydrochlorination is carried out, in which case the AOX decomposition preferably takes place to such an extent that a final a waste water is obtained which either contains only very low amounts of AOX-producing constituents (preferably below 10 mg/1) or in which the content of the AOX-producing substances is reduced to such an extent that it can be subjected to a further biological treatment using microorganisms without any problems in order to finally also decompose the remaining organic compounds in the waste water.

Another advantage of the process according to the invention is that, in principle, any conventional reactor may be used to carry it out, in which case no special measures are needed with respect to the construction of the reactor walls and the possibly existing installations because neither caking nor corrosion problems occur in the process according to the invention.

It was also surprising that, despite the "mild" conditions of the process according to the invention in comparison to the known processes, such as the relatively low temperatures and pressures as well as short residence times, the chlorinated organic residues or by-products from the synthesis of epichlorohydrin can be substantially decomposed thermochemically so that the AOX of a waste water from the synthesis of epichlorohydrin (according to the known process) which typically has values between 25 and 45 mg/liter can be lowered below 10 mg/liter, preferably below 5 mg/liter, and the calcium-chloride-containing solution which remains after the dechlorination and/or dehydrochlorination treatment may be neutralized, and therefore will comply with future legal regulations with respect to the AOX-content of industrial waste waters.

The elimination of AOX-producing components by more than 75%, preferably more than 97%, in the waste water from the synthesis of epichlorohydrin is achieved particularly by means of the advantageous embodiments of the process according to the invention with respect to the setting of the pH-value, the temperature, the pressure and the residence time, whereby it becomes possible to control the AOX-decomposition rates.

Accordingly, in the first process step, the waste water to be treated according to a first preferred embodiment of the process according to the invention has a pH-value of from 11.5 to 12.5 (measured at room temperature) or is adjusted to it, and the dechlorination and/or dehydrochlorination treatment of the chlorinated organic compounds contained in the waste water is carried out in the reactor at a temperature of from 125° to 135° C., a pressure of from 2.5 to 4.0 bar (abs.) and a residence time of the waste water of from 1 to 7 hours.

According to another advantageous embodiment of the process according to the invention, in the first process step, the waste water to be treated has a pH-value of from 13 to 14 (measured at room temperature) or is adjusted to it, and the dechlorination and/or dehydrochlorination treatment of the chlorinated organic compounds contained in the waste water is carried out in the reactor at a temperature of from 125° to 135° C., a pressure of from 2.5 to 4.0 bar (absolute), and a residence time of the waste water of from 1 to 4 hours.

According to another advantageous embodiment of the process according to the invention, in the first process step, the waste water to be treated has a pH-value of from 11.5 to 12.5 (measured at room temperature) or is adjusted to it, and the dechlorination and/or dehydrochlorination treatment of the chlorinated organic compounds contained in the waste water is carried out in the reactor at a temperature of from 175° to 185° C., a pressure of from 9.0 to 10.5 bar (absolute), and a residence time of the waste water of from 1 to 8 hours.

According to yet another advantageous embodiment of the process according to the invention, in the first process step, the waste water to be treated has a pH-value of from 11.5 to 12.5 (measured at room temperature) or is adjusted to it, and the dechlorination and/or dehydrochlorination treatment of the chlorinated organic compounds contained in the waste water is carried out in the reactor at a temperature of from 85° to 90° C., a pressure of from 1.0 to 1.5 bar (absolute), and a residence time of the waste water of from 1 to 7 hours.

According to still another advantageous embodiment of the process according to the invention, in the first process step, the waste water to be treated has a pH-value of from 11.5 to 12.5 (measured at room temperature) or is adjusted to it, and the dechlorination and/or dehydrochlorination treatment of the chlorinated organic compounds contained in the waste water is carried out in the reactor at a temperature of from 155° to 165° C., a pressure of from 5.0 to 7.4 bar (absolute), and a residence time of the waste water of from 4 to 8 hours.

According to the invention, it was found that, also in the case of relatively low temperatures and pressures as well as a pH-adjustment of preferably in the range of from 11.5 to 12.5, high decomposition rates are possible with residence times of less than 10 hours, which represents another advantage of the process according to the invention.

It was also found to be advantageous in the synthesis of epichlorohydrin to use lime water with an excess of calcium hydroxide (relative to the stoichiometric amount of dichloropropanol calculated theoretically for the complete reaction) as the calcium-hydroxide-containing aqueous solution, in which case the excess amount is selected to be so large that the waste water to be treated is already adjusted by the process producing the waste water to pH-values of from 11 to 12.5 (measured at room temperature) and thus, already has the pH-value required for the thermal treatment under alkaline conditions, as soon as it flows out of the synthesis reactor.

In order to adjust the waste water, if necessary, to the pH-values according to the invention (measured at room temperature), a corresponding amount of alkali hydroxide and/or alkaline earth hydroxide, preferably an aqueous sodium hydroxide and/or calcium hydroxide solution may be added.

According to another advantageous embodiment of the process of the invention, the pH-value may also be adjusted by using a corresponding amount of alkali carbonate and/or alkali hydrogen carbonate, preferably an aqueous sodium carbonate and/or sodium hydrogen carbonate solution.

Advantageously, the waste water which was treated in a thermal-alkaline manner is introduced for further treatment into another reactor and is subjected there, in the presence of a hydrogen-containing gas or a compound which releases hydrogen and/or in the presence of a catalytically active substance, to another dechlorination and/or dehydrochlorination treatment. However, the above-mentioned further dechlorination and/or dehydrochlorination treatment may also be carried out in the same reactor use for the thermal waste water treatment under alkaline conditions.

Preferably, high-purity hydrogen (particularly at least 99.9% hydrogen) is used as the hydrogen-containing gas in the process of the invention. However, if necessary, a mixture of hydrogen and an inert gas may also be used.

As the catalytically active substance, a metal, a metal alloy and/or an inorganic and/or organic metal compound or a mixture of substances which contains one or more of these compounds is preferably used, in which case the catalytically active substance is used in the process according to the invention with the addition of a carrier substance, preferably an aluminum-oxide-containing carrier, in that it is, for example, applied to this carrier.

According to another preferred embodiment of the process according to the invention, a palladium-containing compound is used as the catalytically active substance.

Since the waste water flowing out of the synthesis reactor contains suspended solids, primarily undissolved calcium hydroxide (particularly if excess lime water is used as the agent having the alkaline effect in the production of epichlorohydrin), which may lead to disturbances in the treatment process, for example, by forming obstructions, it is advantageous to at least partially free the waste water of the suspended solids. This may optionally be done before, during and/or after the dechlorination and/or dehydrochlorination treatment. The solids may be separated from the waste water by conventional measures. Preferably, this takes place by means of a chemical reaction in that, for example, suspended calcium hydroxide is dissolved by the addition of hydrochloric acid, and/or by means of a mechanical separating process, such as filtration or sedimentation.

The process according to the invention may be carried out in a continuous or discontinuous operation, in which a reactor unit is preferably used which is composed of at least three, particularly four (individual) reactors which are connected in series or in parallel with one another.

Because of the above-mentioned suspended solids which may be present in the waste water, the feeding of the waste water flow to be treated advantageously takes place at the head of the reactor or reactors in a downward-directed flow, and the treated waste water is discharged from the reactor at the bottom. A feeding of the waste water from below into the reaction vessel with an upward-directed flow would lead to clogging problems because of the suspended solids.

However, for the continuous implementation of the dechlorination and/or dehydrochlorination treatment of the waste water, a flow tube or tubular reactor may also be used, in which case, according to another advantageous embodiment of the process according to the invention, a flow velocity of more than 4 m/sec. (meters per second) is established in the flow tube or the tubular reactor. The flow velocity is preferably 8.5 m/sec.

The second process step of the process according to the invention may be carried out in the reactor or reactors which were used for the first process step, in that, after the termination of the first process step which took place, for example, in a discontinuous process, the pretreated waste water remains in the reactor or reactors and while the reagent or reagents are introduced for the further treatment (by way of corresponding feeding devices), the further dechlorination and/or dehydrochlorination treatment is carried out there. If the thermal treatment under alkaline conditions was carried out in a continuous operation, the pretreated waste water flow, after flowing out of the reactor or reactors, can be returned to it or them in order to be subjected there in a continuous or discontinuous process to the further dechlorination and/or dehydrochlorination treatment.

However, according to another embodiment of the process according to the invention, the waste water treated in the first process step can also be discharged from the reactor or reactors and can then be charged into at least one additional reactor for treatment according to the second process step.

For a catalytic treatment of the waste water in the second process step, a fixed-bed reactor or a fluid bed reactor, preferably a fluidized-bed reactor, may, for example, be used in this case.

Since clogging problems caused by suspended solids may also occur in the reactor used for the further treatment of the waste water, the waste water is advantageously freed of suspended solids before a further dechlorination and/or dehydrochlorination treatment, preferably by a chemical reaction and/or mechanical separating processes which may, for example, correspond to those described above.

Furthermore, it may be advantageous, to optionally cool the waste water before the further treatment and/or to adjust the pH.

According to another embodiment of the process according to the invention, the treatment of the waste water according to the first process step may be repeated at least once.

The flow of waste water to be treated according to the invention may be heated to the treatment temperatures using conventional heating devices, in which case, electric energy or thermal energy, for example, accumulated in hot steam, may be used for the heating.

In order to further improve the energy balance of the process according to the invention, it is advantageous to transfer the thermal energy accumulated in the heated, treated and possibly further-treated waste water flow at least partially to a cooler waste water flow which is still to be treated, in which case the hot treated waste water flow is cooled at the same time. For this purpose, a heat exchanger is used through which the treated and possibly further-treated waste water flows after the discharge from the dechlorination or dehydrochlorination reactor or reactors.

Preferably, the heat transfer takes place by a direct transfer of thermal energy by way of expansion and condensation, in that the pressure on the hot treated waste water is released, thereby producing steam which is introduced into a cooler waste water stream which is still to be treated and transfers its thermal energy to it by means of condensation.

According to another advantageous embodiment of the process according to the invention, the direct transfer of thermal energy is carried out in at least two steps, preferably in three steps.

During and/or after the heat-up phase of the treatment process according to the invention, gases and/or vapors are released in the waste water to be treated, particularly water vapor charged with the more volatile organic compounds. According to a preferred embodiment of the process of the invention, these gases and/or vapors are returned to the preceding process in which the waste water was produced, e.g., to the epichlorohydrin synthesis reactor.

Preferably, the waste water from the synthesis of epichlorohydrin to be treated by the process of the invention will have a total content of dissolved organic substances of more than 0.15 g/liter.

Furthermore, the waste water treated in the dechlorination process and/or dehydrochlorination process according to the invention, preferably after a cooling, can be subjected to another cleaning, preferably a biological treatment with the use of microorganisms. The decrease in the AOX of the waste water from the synthesis of epichlorohydrin which is achieved in accordance with the initial steps of the present invention, makes it possible to carry out subsequent biochemical or biological decomposition of the remaining organic compounds by means of bacteria. As a result of this microbial decomposition due to the metabolic activity of the microorganisms, the COD-value of the waste water is simultaneously lowered due to the destruction of the organic compounds dissolved in the waste water (which originate as secondary products from the dechlorination or dehydrochlorination process or as by-products from the epichlorohydrin synthesis).

According to another embodiment of the process according to the invention, the waste water discharged from the reactor after thermal treatment under alkaline conditions, may also be introduced directly to a biological treatment.

The biological treatment may be carried out in an aerobic or anaerobic operation.

Before biological treatment, the pH of the waste water may optionally be appropriately adjusted in order to render the waste water susceptible to microbiological treatment.

In addition, the present invention relates to an apparatus for dechlorination and/or dehydrochlorination treatment of waste water which contains chlorinated organic compounds from the production of epichlorohydrin, whereby the treatment preferably takes place in accordance with the process of the invention.

The apparatus according to the invention provides a facility which can be used on a large-scale basis and in which waste water can be economically dechlorinated and/or dehydrochlorinated in an optimum manner. It is also advantageous that the apparatus according to the invention can make use of standard equipment.

It has now been found that an apparatus comprising at least one separator, at least one heating device 9, at least one heat exchanger 8 and at least one reactor, preferably a reactor unit consisting of at least three reactors connected behind or in parallel, has the aforementioned advantages. In particular, if at least three, and preferably four, dechlorination or dehydrochlorination reactors are used, the apparatus according to the invention facilitates optimization of the AOX decomposition rate as well as minimizing the operating and system costs required to carry out the process of the invention in continuous or batch operation.

In accordance with a preferred embodiment of the apparatus according to the invention, a sedimentation separator is used as the separator 2 by means of which suspended solids are at least partially removed from the waste water as by the effect of gravitational force. Use of such a separator is desirable because a settling of solids in the heat exchanger and/or the reactor or reactors may lead to clogging or an accumulation of mud in the above-mentioned equipment and thus to operational disturbances so that operational interruptions may occur in order to carry out purification processes for the removal of deposits of solid matter.

Conventional settling equipment may be used as sedimentation separators, which may be operated intermittently or continuously.

Furthermore, the settling apparatuses are preferably equipped with a raking unit which is arranged on a center shaft in the sedimentation vessel. According to a preferred embodiment of the arrangement according to the invention, the rotational speed of the raking unit amounts to less than 2.5 rpm, preferably 1.5 rpm, whereby the water is kept in motion in order to avoid deposition of the sedimenting solids in the separator.

Conventional reaction vessels or reaction columns may be used as the reactors, in which case these may also be equipped with a stirring unit for thoroughly mixing the waste water. The reactor walls advantageously consist of unalloyed steel since no corrosion problems occur in the waste water treatment process according to the invention.

Preferably, the separator 2 and/or the reactor or each individual reactor 4, 5, 6 has a conical shape. It is particularly advantageous if the respective reaction vessels and/or the settlement vessel has a conical lower portion.

In order to prevent clogs or deposits in the separator 2 and/or the reactor or in each individual reactor 4, 5, 6, according to another preferred embodiment of the apparatus of the invention, the above-mentioned apparatuses each have a cone angle of less than 120°, preferably 90°.

In order to produce advantageous flow characteristics, according to another preferred embodiment of the apparatus of the invention, the dimensions of the separator 2 and/or of the reactor or of each individual reactor 4, 5, 6 are selected such that, in each of the above-mentioned devices, the ratio of the total height to the diameter of the reaction or settling vessel is greater than 2.0, preferably about 2.5.

When the dimensions are related to the ratio of the cylindrical height to the diameter of the separator 2 and/or of the reactor or each individual reactor 4, 5, 6, this ratio is greater than 1.4, preferably about 1.7.

The preheating and heating of the waste water to be treated to the dechlorination or dehydrochlorination temperatures according to the invention takes place in conventional heating devices.

After the first treatment cycle, a direct or indirect preheating of the incoming stream, which follows, of a still untreated waste water can take place by means of the hot outflowing current of the treated waste water, in which case at least a portion of the accumulated thermal energy is transferred to the cooler waste water flow still to be treated, whereby the treated waste water leaving the reaction zone is simultaneously cooled.

For this purpose, one or more heat exchangers are used which may be of conventional construction and may be arranged in one or more stages.

Furthermore, the apparatus according to the invention may comprise another reactor 7 for carrying out the dechlorination and/or dehydrochlorination treatment according to the second process step. Preferably, a fixed-bed reactor or a fluid bed reactor, particularly a fluidized-bed reactor, is used in this case.

According to another preferred embodiment of the apparatus according to the invention, the reactor or each individual reactor 4, 5, 6, 7 is in each case equipped with at least one inlet conduit for the hydrogen-containing gas or the hydrogen-releasing compound and/or the catalytically active substance. For charging the waste water with the hydrogenous gas, for example, at least one spray tower or at least one injector system may be used.

DETAILED DESCRIPTION OF THE DRAWING

Figure 1:
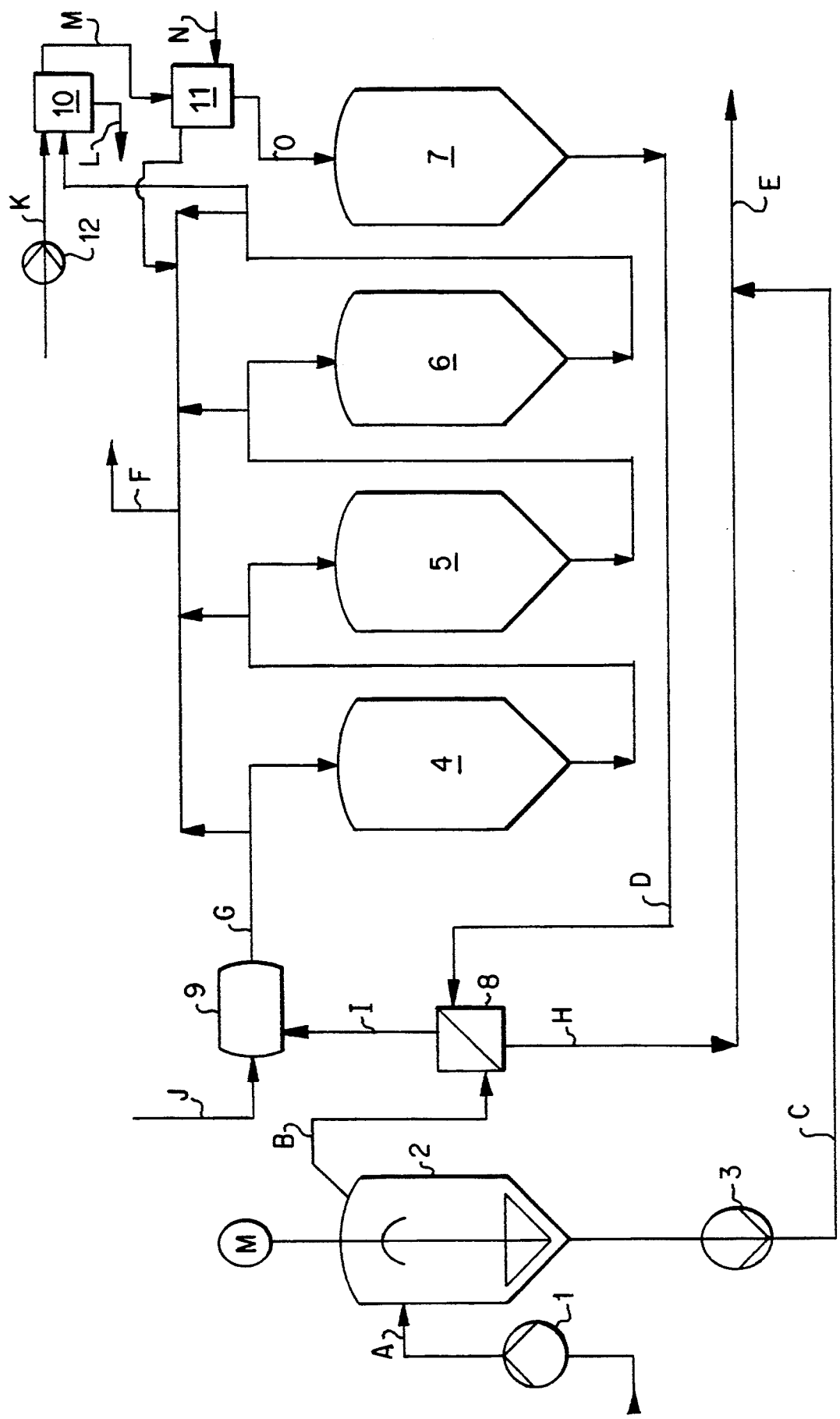
FIG. 1 illustrates a possible apparatus for carrying out the process of the invention and a schematic flow chart of a preferred implementation of the process.

FIG. 1 relates to a continuous process. Waste water from the epichlorohydrin synthesis reactor (not shown in the drawing) which is to be treated, is fed by a pump 1 and a feed line A into a sedimentation separator 2 in which the waste water is at least partially freed of suspended solids. Using another pump 3, the draining of the bottom product of the sedimentation separator takes place by way of a drain C. Via another drain B, the clear flow of the sedimentation separator in the upper part of the settling apparatus is drained.

Then (if a first treatment cycle for a waste water flow has already been carried out and a hot treated waste water flow is available), the waste water will pass through a heat exchanger 8 where the heat of an already treated waste water flow is transferred to the untreated incoming flow so that an energy-saving preheating of the waste water is carried out. The hot waste water flow which acts as an energy carrier arrives by way of the feed pipe D in the heat exchanger and, after the energy transfer, which results in a cooling of the treated waste water flow, is drawn off by way of the drain H from the heat exchanger and is guided to a drain E for the further treatment and/or use of the waste water.

The further heating of the untreated waste water flow to the final dechlorination or dehydrochlorination temperature takes place in a heating device 9 which is connected with the heat exchanger by way of a pipe I. Hot steam may, for example, be used as the heating medium which is supplied to the heating device by way of the feed pipe J.

Subsequently, the heated waste water is fed by way of the feed pipe G, into the three dechlorination and/or dehydrochlorination reactors 4, 5, 6 which are connected in series, in which case the untreated waste water enters at the head of each of the reaction vessels and is discharged by means of a respective outlet in the lower part of the reactors. The operation of the reactor takes place in a flooding manner. The waste water remains in the reactors corresponding to the desired residence time and is fed, after the end of the treatment time, into a separator 10 for solids in which by the addition of hydrochloric acid, the waste water is adjusted to such a pH-value that suspended calcium hydroxide is at least partially dissolved. Remaining solids are separated from the waste water and are discharged from the separator for solids by way of a drain L. The feeding of the hydrochloric acid takes place by way of pipe K by means of a pump 12. By way of pipe M, the waste water arrives in a spray tower 11 and is charged there with gaseous hydrogen which arrives in the spray tower by way of feed pipe N. The waste water—hydrogen mixture is fed by way of pipe O into the reactor 7 which is preferably designed as a fluidized-bed reactor, and here the waste water is subjected to another dechlorination and/or dehydrochlorination treatment. After the end of the treatment, the waste water is fed to the heat exchanger 8 by way of drain D.

Before or after the treated waste water passes through or has passed through the heat exchanger, a further separation of suspended solids from the treated waste water flow may take place. This also preferably takes place in a sedimentation separator.

During the heating and during the treatment of the waste water, gases or vapors are formed which are preferably separated from the waste water flow and are returned, by way of a pipe F, for example, into the reactor of the epichlorohydrin synthesis.

Furthermore, the bottom product drain C of the sedimentation separator 2 may be used for adjusting the pH-value of the treated waste water flow E in such a manner that the waste water can subsequently be subjected to a microbiological treatment.

The following working examples are intended to illustrate the invention in further detail without limiting its scope.

Example 1

One liter of a waste water from the production of epichlorohydrin having an AOX-content of approximately 35 mg/liter and a pH-value of 12 (measured at room temperature) was subjected to thermal dechlorination or dehydrochlorination treatment according to the invention under alkaline conditions in a reactor for 3 hours at a temperature of 85° C. and a pressure of 1 bar (abs.). As a result, the AOX-content of the waste water was decreased by approximately 30%.

Subsequently, the waste water was adjusted to a pH-value of 10 by addition of hydrochloric acid, and remaining solids were separated by sedimentation. Then, the waste water was treated in a fluidized bed in the presence of hydrogen and of a palladium-containing catalyst for one hour at room temperature. As a result, the AOX-content of the waste water was decreased by 83%.

Example 2

One liter of a waste water from the production of epichlorohydrin having an AOX-content of approximately 35 mg/liter and a pH-value of 12 (measured at room temperature) was subjected to thermal dechlorination or dehydrochlorination treatment according to the invention in a reactor under alkaline conditions for 5 hours at a temperature of 130° C. and a pressure of 2.5 bar (abs.). As a result, the AOX-content of the waste water was decreased by approximately 66%.

Subsequently, the waste water was adjusted to a pH-value of 10 by addition of hydrochloric acid, and remaining solids were separated by sedimentation. Then, the waste water was treated in the presence of hydrogen and a palladium-containing catalyst in a fluidized bed for one hour at room temperature. As a result, the AOX-content of the waste water was decreased by 91%.

Example 3

One liter of a waste water from the production of epichlorohydrin was subjected to thermal treatment under alkaline conditions in a manner analogous to Example 2, and was subsequently adjusted to a pH-value of 10.5 by addition of hydrochloric acid, cooled and subjected to an aerobic biological treatment at 20° C. with an average residence time of 10 hours. As a result, the AOX-content of the waste water was decreased by approximately 75%, and the COD-value was decreased by approximately 85%.

Example 4

One liter of a waste water from the synthesis of epichlorohydrin was subjected to thermal treatment under alkaline conditions in the presence of a catalyst in a manner analogous to Example 2, and was then subjected to an aerobic biological treatment at 26° C. with an average residence time of 7 hours. As a result, the COD-value was decreased by more than 85%.

The foregoing description and examples have been set forth merely to illustrate the invention and are not intended to be limiting. Since modifications of the disclosed embodiments incorporating the spirit and substance of the invention may occur to persons skilled in the art, the invention should be construed to include all variations within the scope of the appended claims and equivalents thereof.

What is claimed is:

1. A process for treating a liquid containing more than 10 mg of adsorbable organic halogen compounds (AOX) per liter comprising the steps of
introducing said liquid at a pH of 10 to 14 (measured at room temperature) into a reactor and in a first treatment step maintaining a temperature of at least 75° C., a pressure of at least 1 bar (abs.) and a residence time of at least 0.5 hours in said reactor, thereby partially dechlorinating or dehydrochlorinating chlorinated organic compounds contained in the liquid;
subsequently subjecting said liquid in a second treatment step to a further dechlorination or dehydrochlorination treatment in the presence of a hydrogen-containing gas, a compound which releases hydrogen or a catalytically active substance, and discharging the treated liquid.

2. A process according to claim 1, further comprising subjecting the liquid after said further dechlorination or dehydrochlorination treatment to a biological purification treatment with microorganisms.

3. A process according to claim 1, wherein said liquid is waste water from the production of epichlorohydrin.

4. A process according to claim 1, further comprising adjusting the pH of said fluid to a value of from 10 to 14 prior to said introducing step.

5. A process according to claim 1, wherein said liquid is thermally treated in said first treatment step at a temperature of from 85° to 185° C. and a pressure of from 2 to 10.5 bar (abs.), with a residence time of from 1 to 8 hours, and said second treatment step is carried out in the presence of substantially pure hydrogen, a metal, a metal alloy, an inorganic or organic metal compound, or a mixture of at least two of the foregoing substances.

6. A process according to claim 1, wherein said second treatment step is carried out in the presence of a catalytically active palladium-containing compound deposited on a carrier.

7. A process according to claim 6, wherein said carrier is an aluminum-oxide-containing carrier.

8. A process according to claim 1, wherein said liquid is waste water containing at least 0.15 g/liter of dissolved halogen-containing organic compounds.

9. A process according to claim 1, wherein said second treatment step is carried out in a series of at least 3 tubular reactors and wherein said liquid flows through said tubular reactors at a flow velocity of at least 4 meters per second.

10. A process according to claim 9, wherein said second treatment step is carried out in a series of 4 tubular reactors.

11. A process according to claim 9, wherein said liquid flows through said tubular reactors at a flow velocity of at least 8.5 meters per second.

12. A process according claim 1, further comprising the step of at least partially freeing said liquid of suspended solids.

13. A process according to claim 12, wherein said liquid is at least partially freed of suspended solids by chemical treatment.

14. A process according to claim 12, wherein said liquid is at least partially freed of suspended solids by mechanical filtration.

* * * * *